United States Patent
Bhushan et al.

(10) Patent No.: US 11,465,327 B1
(45) Date of Patent: Oct. 11, 2022

(54) FRACTIONAL LOBE PROCESSOR

(71) Applicant: STEERLIFE INDIA PRIVATE LIMITED, Bengaluru (IN)

(72) Inventors: Indu Bhushan, Bengaluru (IN); Vinay Rao, Bengaluru (IN); Vijay Kulkarni, Bengaluru (IN); Chetan Chincholi, Bengaluru (IN); Aravind Kumar Gurram, Bengaluru (IN); Babu Padmanabhan, Bengaluru (IN)

(73) Assignee: STEERLIFE INDIA PRIVATE LIMITED, Bengaluru (IN)

( * ) Notice: Subject to any disclaimer, the term of this patent is extended or adjusted under 35 U.S.C. 154(b) by 550 days.

(21) Appl. No.: 15/760,583

(22) PCT Filed: Apr. 24, 2017

(86) PCT No.: PCT/IB2017/052335
§ 371 (c)(1),
(2) Date: Mar. 15, 2018

(87) PCT Pub. No.: WO2017/183007
PCT Pub. Date: Oct. 26, 2017

(30) Foreign Application Priority Data

Apr. 22, 2016 (IN) .............................. 201641014096
Apr. 22, 2016 (IN) .............................. 201641014167

(51) Int. Cl.
*B29C 48/655* (2019.01)
*A61K 9/14* (2006.01)
(Continued)

(52) U.S. Cl.
CPC ............ *B29C 48/655* (2019.02); *A61K 9/146* (2013.01); *A61K 31/216* (2013.01);
(Continued)

(58) Field of Classification Search
CPC .............................. B29C 48/655; B29C 48/83
See application file for complete search history.

(56) References Cited

U.S. PATENT DOCUMENTS 4,127,331 A * 11/1978 Herbert ................... B29C 48/83
366/83
4,422,992 A * 12/1983 Michel .................. B29C 48/022
264/108

(Continued)

FOREIGN PATENT DOCUMENTS

WO    WO 2014192026    12/2014

OTHER PUBLICATIONS

Ch 10 of Tadmor, Z. and Gogos, C.G., 2006. Principles of polymer processing. (Year: 2006).*
(Continued)

*Primary Examiner* — Nicholas R Krasnow
(74) *Attorney, Agent, or Firm* — Troutman Pepper Hamilton Sanders LLP (Rochester)

(57) ABSTRACT

A fractional lobe processor comprises a barrel with heating and cooling means having two parallel intersecting bores of equal diameter, wherein the centre distance between the two bores is lesser than the diameter of the bore; a shaft coupled with a plurality of screw elements to form a screw within each bore, wherein the screws are intermeshing and form at least three zones within the barrel, the zones comprising an intake zone comprising at least one deep flighted shovel element on each intermeshing screw for receiving a feed comprising an active substance and/or an excipient, a melt zone consisting of only fractional lobe elements for melting the active substance and/or an excipient to form a viscous mass or melt, and a discharge zone, wherein the melt zone
(Continued)

is located before the discharge zone and after the intake zone; and wherein the melt zone has a plurality of fractional lobe elements on each shaft.

11 Claims, 9 Drawing Sheets

(51) Int. Cl.
 *A61K 31/216* (2006.01)
 *B29C 48/68* (2019.01)
 *B29C 48/80* (2019.01)
 *B29C 48/40* (2019.01)

(52) U.S. Cl.
 CPC ............ *B29C 48/402* (2019.02); *B29C 48/68* (2019.02); *B29C 48/83* (2019.02)

(56) References Cited

U.S. PATENT DOCUMENTS

| | | | |
|---|---|---|---|
| 5,587,434 A * | 12/1996 | McCullough, Jr. | C08F 8/00 525/333.8 |
| 6,318,650 B1 | 11/2001 | Breitenbach | |
| 6,783,270 B1 * | 8/2004 | Padmanabhan | B29B 7/489 366/82 |
| 7,910,030 B2 | 3/2011 | Remon et al. | |
| 8,231,375 B2 | 7/2012 | Remon et al. | |
| 2001/0011067 A1 * | 8/2001 | Allan | C11D 17/0069 510/152 |
| 2001/0041169 A1 * | 11/2001 | Allan | B29C 48/297 424/65 |
| 2006/0069228 A1 * | 3/2006 | McCloskey | B29C 48/76 528/196 |
| 2007/0161719 A1 * | 7/2007 | Rauh | C08J 11/12 521/40 |
| 2008/0056058 A1 * | 3/2008 | Padmanabhan | B29C 48/49 366/85 |
| 2011/0110183 A1 * | 5/2011 | Bierdel | B29C 48/2517 366/301 |
| 2014/0036614 A1 * | 2/2014 | Padmanabhan | B29C 48/57 366/85 |
| 2014/0080951 A1 | 3/2014 | Raman et al. | |
| 2016/0082640 A1 | 3/2016 | Padmanabhan | |
| 2016/0244573 A1 * | 8/2016 | Roden | B29C 48/507 |
| 2016/0279828 A1 | 9/2016 | Padmanabhan | |
| 2018/0161777 A1 * | 6/2018 | Thomas | B02C 4/08 |
| 2019/0134875 A1 * | 5/2019 | Bhushan | B29B 9/08 |

OTHER PUBLICATIONS

International Search Report received in PCT/IB2017/052335, dated Sep. 6, 2017, 2 pages.
Written Opinion received in PCT/IB2017/052335, dated Sep. 6, 2017, 7 pages.

* cited by examiner

| Cross section | ISO-3D-View (wire frame) | Description |
|---|---|---|
|  |  | Fractional Kneading Block (FKB) |
|  |  | Continuous Mixing Element (CME) |
|  |  | Fractional Mixing Element (FME) |
|  |  | 3Lobe Right hand Screw Element (3RSE) |

| | | |
|---|---|---|
|  |  | 3Lobe Left hand Screw Element (3LSE) |
|  |  | Special Shovel Type Element (SSV) |
|  |  | (Special Shovel to 3RSE) Transition Element (SSV-3RSE) |
|  |  | Right handed Fractional Kneading Block (RFKB) |
|  |  | Dynamic Stir Element (3DSA) |
|  |  | Eccentric Fractional Kneading Block (EKB) |

FRACTIONAL LOBE PROCESSOR

FIELD OF THE INVENTION

The present invention relates to a Fractional Lobe Processor and its applications.

BACKGROUND OF THE INVENTION

Depending on the product specifications there are several inherent technical challenges to continuous manufacturing. In pharmaceuticals, for example, powder characterization and handling, dosage forms with low drug loading, process modeling. Other challenges include build-up of material over long run times in the processing vessels, feeding of cohesive materials, material tracking through system, controlling particle size distribution of the output etc.

In pharmaceuticals, continuous manufacturing is consistent with FDA's Quality by Design (QbD) efforts. It is a modern manufacturing approach with potential to improve assurance of quality and consistency of dosage forms. There is clearly a strong need to move the manufacturing of pharmaceutical products from the current batch, to better continuous processing.

Twin-screw processors are versatile devices that allow work to be done efficiently on materials in a continuous manner. Work done on the material is the result of application of shear forces, extensional forces that cause elongation or stretching of material, compressive forces that result in pressure build-up and squeezing of the material and bending forces that cause fibres and layers to fold and interact. However, current integer lobe twin screw processors which have a screw configuration made up entirely of integer-lobed elements, cannot prevent the material being processed from the effects of a combination of all these types of work. For example, in certain situations, it may not be desirable to subject the material to extensional forces or to compressive forces. The extensional forces or to compressive forces occur in three-dimensional space inside the processor defined by axial and longitudinal plane for each screw in addition to several radial planes. Flow of the material between elements in different radial planes creates lateral shear in the material being processed. In general, the radial and lateral shear rates are 10 to 100 times greater in magnitude compared to axial or longitudinal shear stress. Radial and lateral shear are not experienced uniformly by all particles in the material being processed. Another example, is in case of processes like hot melt extrusion, sometimes the shear imparted to the material being processed is not uniform. Stagnation of material during processing in the twin screw processor, is another problem with bilobed elements. For mixing, when the screw geometry transitions from conveying to kneading, it results in material accumulation in that section of the barrel and stagnation occurs. This adversely affects the heat transfer and physical movement of the material and ultimately its degradation.

PCT application number PCT/IN2014/000358 discloses a continuous one-pot process carried out in a twin-screw processor for preparation of solid dosage forms. Further, the U.S. Pat. Nos. 6,318,650, 7,910,030 and 8,231,375 also disclose continuous processes. There is however a need to improve upon the processes disclosed in the publications.

Besides, as well known in the art, twin screw processors and processes are quite unpredictable, due to several independent and dependent variables like screw speed, feed rate, barrel temperature, torque, product temperature, residence time, etc and there is still a need to develop accurate solutions for predicting the optimum process parameters or the product attributes of the output. U.S. Pat. No. 6,783,270, US2014/0036614 A1 and US2016/0279828 A1 discuss the fractional geometry of screw elements. However, the optimal utilization of the potential of these elements in various applications for developing or engineering optimized processes to obtain desired product attributes is discussed in detail in the disclosure below.

BRIEF DESCRIPTION OF DRAWINGS

FIGS. 5A, 5C, and 5D are results of Comparative Examples 1-3 showing particle size distribution of multiparticulates after hot melt fragmentation in a Twin Screw Processor without fractional elements. FIGS. 5B, 5D, and 5F are results of Examples 1-3 showing particle size distribution of multiparticulates after hot melt fragmentation in a Fractional Lobe Processor.

SUMMARY OF THE PRESENT INVENTION

Figure 1A:
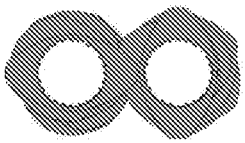
FIGS. 1A and 1B depict designs designs of various types of Fractional Lobe Elements.
Figure 1A:
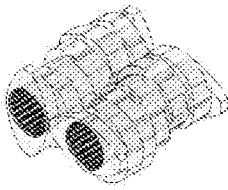
Figure 1A:
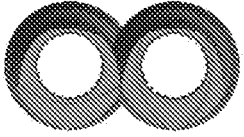
Figure 1A:
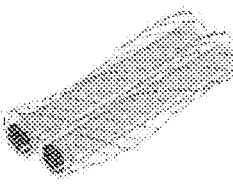
Figure 1A:
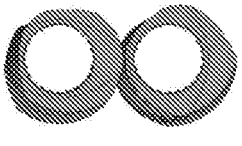
Figure 1A:
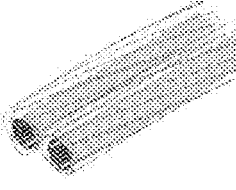
Figure 1A:
Figure 1A:
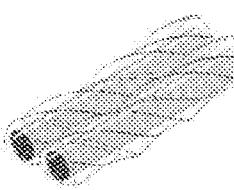
Figure 1B:
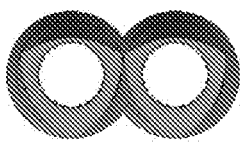
Figure 1B:
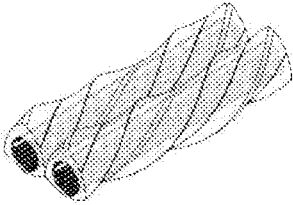
Figure 1B:
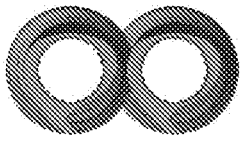
Figure 1B:
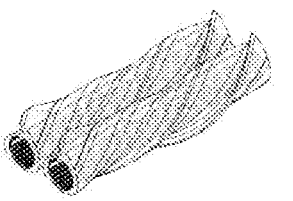
Figure 1B:
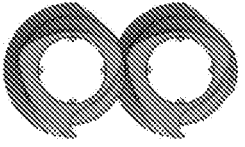
Figure 1B:
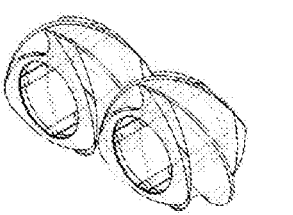
Figure 1B:
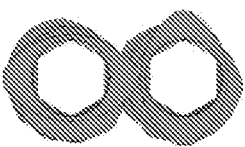
Figure 1B:
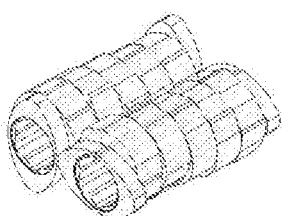
Figure 1B:
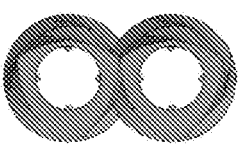
Figure 1B:
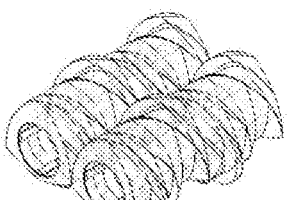
Figure 1B:
Figure 1B:
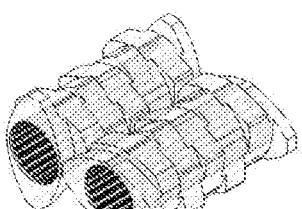

A fractional lobe processor is disclosed. The fractional lobe processor comprises:
  a barrel with heating and cooling means having two parallel intersecting bores of equal diameter, wherein the centre distance between the two bores is lesser than the diameter of the bore;
  a shaft coupled with a plurality of screw elements to form a screw within each bore, wherein the screws are intermeshing, and wherein the screws form at least three zones within the barrel, the zones comprising:
  i. an intake zone comprising at least one deep flighted shovel element on each intermeshing screw for receiving a feed comprising an active substance and/or an excipient;
  ii. a melt zone consisting of only fractional lobe elements for melting the active substance and/or an excipient to form a viscous mass or melt; and
  iii. a discharge zone; wherein the melt zone is located before the discharge zone and after the intake zone; and wherein the melt zone has a plurality of fractional lobe elements on each shaft.

DETAILED DESCRIPTION

The present disclosure relates to a Fractional Lobe Processor. A Fractional Lobe Processor is a next generation co-rotating twin-screw processor characterized by, predominantly fractional geometry in the screw configuration in its melt zone.

In a main embodiment, the disclosure relates to a fractional lobe processor comprising
  a. a barrel with heating and cooling means having two parallel intersecting bores of equal diameter, wherein the centre distance between the two bores is lesser than the diameter of the bore;

b. a shaft coupled with a plurality of screw elements to form a screw within each bore, wherein the screws are intermeshing, and wherein the screws form at least three zones within the barrel, the zones comprising
   i. an intake zone comprising at least one deep flighted shovel element on each intermeshing screw for receiving a feed comprising an active substance and/or an excipient;
   ii. a melt zone consisting of only fractional lobe elements for melting the active substance and/or an excipient to form a viscous mass or melt; and
   iii. a discharge zone;
wherein the melt zone is located before the discharge zone and after the intake zone; and
wherein the melt zone has a plurality of fractional lobe elements on each shaft.

The intake zone has one or more pairs of deep flighted shovel elements which aid in intake of feed continuously. The term "deep flighted shovel" can be understood with respect to the elements as per disclosure in US2008/0056058 A1.

The screw flights of such elements are designed to plough through the material similar to the working of a snowplough. The shovel elements are required in the intake zone in the screw configuration having fractional lobe elements which have a greater forward conveying ability. Especially in case of powders the shovel elements increase the intake capacity of the processor. The examples of such shovel elements are - Regular Flight Shovel Element (RFV), Single Flight Shovel Element (SFV), Right Handed Shovel Element (RFV), SSV and SSV3RSE. Also, some transition elements can be used with shovel elements, such as RFN: Right Handed Transition Element. The SSV is a tri-lobe type of shovel element used for high volume conveying. The SSV-3RSE is a transition element that is usually used as a bridge between the SSV and 3RSE elements in the element assembly to provide a smooth flow of material.

The Fractional Lobe Processor is useful for continuous processes such as melt granulation, hot melt fragmentation and hot melt extrusion. It has a modular design for barrels and screws. FLP has interchangeable elements, due to which, each individual screw section can be designed to perform specific functions such as; conveying, mixing, shearing, or pressure building, thus allowing precise control of conditions along the screw length. The FLP provides significant improvement in building both temporal and spatial control in engineering the process through removal of hot spots and dead zones while maintaining seamless process continuity. For temporal and spatial control, a fractional lobe processor is characteristically made up of different zones through which the feed or material is transferred sequentially. The zones represent sections of the screw configuration designed to perform a specific function like conveying, melting, mixing, fragmenting, granulation and the like. The effectiveness of these specific functions largely depends on geometry of the screw elements and the length of the zones. By proper placement of Fractional Lobe Element(s) [FLE(s)] either individually, or in combination in the processing zone/s of the FLP, it is possible to subject the material to only a specific type of work. The amount of work done on the material can also be manipulated by control on movement of material through carefully crafted screw configuration of the processing zones of the FLP while simultaneously manipulating the screw speed, barrel temperature and barrel length.

The type of the FLE(s) used depends upon the attributes of the processed material desired. The FLE's as per this disclosure include- Fractional Kneading Block (FKB), a Right handed Fractional Kneading Block (RFKB), Eccentric Fractional Kneading Block (EKB), Continuous Mixing Element (CME), 3Lobe Right Hand Screw Element (3RSE), 3Lobe Dynamic Stir Element (3DSA) and Melt Formation Element (MFE).

The FKB is a 90° left hand twist kneading block element with fractional segments in middle, with bi-lobed segments on either ends for the ease of assembly. It provides high smearing action for melting. It provides high melting efficiency, induced melt-mixing and uniform and intense shear. The RFKB is a 90° right hand twist kneading block element with fractional segments in middle, with bi-lobed segments on either ends for the ease of assembly. It provides high smearing action for melting. The EKB is 90° right hand twist kneading block element with bi-lobed segments on either ends for the ease of assembly and eccentric fractional tri-lobe segments in middle. It provides highest level of shear uniformity with low shear intensity. The CME is a cherry-blossom type fractional five lobed element. It is usually used in as set of forward (right hand) and reverse (left hand) element in assembly to form a perfect combination for efficient mixing. The element has a bi-lobe profile step on one side. It provides high Shear intensity and uniformity. It is used for dispersive mixing. The 3RSE is a specially designed (1.3.80 ratio) tri-lobe type of forward conveying element. The 3DSA is a specially designed (1.3.80 ratio) tri-lobe dynamic stir element promoting forward mixing and conveying. The MFE is a special type of element with the 3DSA segments smoothly twisted along the length for longer leads. It helps in promoting stress free high efficiency melting, while eliminating 90° exposure of segments to solids (as in case of regular kneading elements). The MFE creates turbulence to the melt flow without stagnation and material re-agglomeration.

The present disclosure also relates to processes for preparation of extrudates or multiparticulates.

The term "active substance" as used herein means an active pharmaceutical ingredient or the main ingredient of the product of the process and excludes styrene and polyphenylene ether.

The term "excipient" as used herein means a substance which can be processed with the active substance in the processor and excludes styrene and polyphenylene ether.

The disclosure relates to following main embodiments—
In a main embodiment, the disclosure relates to a fractional lobe processor comprising
   a. a barrel with heating and cooling means having two parallel intersecting bores of equal diameter, wherein the centre distance between the two bores is lesser than the diameter of the bore;
   b. a shaft coupled with a plurality of screw elements to form a screw within each bore, wherein the screws are intermeshing, and wherein the screws form at least three zones within the barrel, the zones comprising
      i. an intake zone comprising at least one deep flighted shovel element on each intermeshing screw for receiving a feed comprising an active substance and/or an excipient;
      ii. a melt zone consisting of only fractional lobe elements for melting the active substance and/or an excipient to form a viscous mass or melt; and
      iii. a discharge zone; wherein the melt zone is located before the discharge zone and after the intake zone;

and wherein the melt zone has a plurality of fractional lobe elements on each shaft.

In an aspect, the disclosure relates to the fractional lobe processor as per above embodiment, wherein the melt zone comprises of at least two different fractional lobe elements on each intermeshing screw.

In an aspect, the disclosure relates to the fractional lobe processor as per the main embodiment, wherein between the melt zone and the discharge zone, the screws form a zone that comprises of a plurality of 3lobe right hand screw elements on each intermeshing screw.

In an aspect, the disclosure relates to the fractional lobe processor as per the main embodiment, wherein at least one-third of each intermeshing screw comprises of fractional lobe elements from intake zone to the discharge zone.

In an aspect, the disclosure relates to the fractional lobe processor as per the main embodiment, wherein at least one of the fractional elements in the melt zone has a first lobe defining a first tip angle, a second lobe defining a second tip angle, and a third lobe defining a third tip angle that is different from the first tip angle and the second tip angle.

In an aspect, the disclosure relates to the fractional lobe processor as per the main embodiment, wherein at least one of the fractional elements in the melt zone has a continuous flight helically formed thereon having a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L'.

In an aspect, the disclosure relates to the fractional lobe processor as per the main embodiment, wherein at least one of the fractional elements in the melt zone has a lead 'L' and at least one continuous flight helically formed thereon and, wherein the flight transforms at least once from a first non-integer lobe flight into a second non-integer lobe flight in a fraction of the lead 'L' and transforms back to the first non-integer lobe flight in a fraction of the lead 'L.'

In another embodiment, the disclosure relates to a method of hot melt extrusion comprising the steps of:
a) introducing a feed comprising an active substance and/or an excipient into the intake zone of the fractional lobe processor;
b) passing the feed through a melt zone consisting of only fractional elements, which is set at a temperature above the melting or softening temperature of the active substance and/or the excipient for melting the active substance and/or an excipient to form a viscous mass or melt;
c) passing the viscous mass or melt through a discharge zone towards a die located at the end of the discharge zone;
d) extruding the viscous mass or melt through the die.

In an aspect, the disclosure relates to the method of hot melt extrusion according to preceding embodiment, wherein the fractional lobe processor has a screw configuration such that the intake zone comprises one or more elements selected from a group consisting of SSV and SSV-3RSE elements and the melt zone comprises one or more elements selected from a group consisting of 3DSA, MFE and FKB.

In another embodiment, the disclosure relates to a method of hot melt fragmentation comprising the steps of:
a) introducing a feed comprising active substance and/or an excipient into the intake zone of the fractional lobe processor;
b) passing the feed through a melt zone consisting of only fractional elements, which is set at a temperature above the melting or softening temperature of the active substance and/or the excipient for melting the active substance and/or the excipient to form a viscous mass;
c) passing the viscous mass through a fragmenting zone for simultaneously cooling and fragmenting the viscous mass inside the barrel to form cooled multiparticulates;
d) passing the cooled multiparticulates through the discharge zone towards the exit located at the end of the discharge zone; and
e) collecting the cooled multiparticulates.

In an aspect, the disclosure relates to the method of hot melt fragmentation according to preceding embodiment, wherein the fractional lobe processor has a screw configuration such that the intake zone comprises one or more elements selected from a group consisting of SSV and SSV-3RSE elements and the melt zone comprises one or more elements selected from a group consisting of 3DSA, MFE and FKB.

In an aspect, the disclosure relates to A process for preparation of a population of multiparticulates having the particle size distribution such that more than 75% particles are in the size range of 150-850 µ, less than about 10% of the particles are of size greater than 850 µ and less than 15% of the particles are of size less than 150 µ; by the method of hot melt fragmentation, by a hot melt fragmentation process according to the preceding embodiment.

Hot Melt Fragmentation

Hot melt fragmentation is a method of forming fragments within a co-rotating twin screw processer comprising feeding one or more excipient(s) into the extruder; softening or melting at least one excipient to form a viscous mass or melt; and simultaneously fragmenting and cooling the viscous mass or melt to obtain cooled fragments followed by collecting the cooled fragments from the extruder.

The hot melt fragmentation process results in formation of fragments which are collected as an output in the form of multiparticulates. It would be highly desirable to have an output with a controlled particle size distribution, so that further processing or size reduction and sieving can be avoided. Generally, particle size distribution of a population of particles determines how particles pack together, and hence will influence its properties such as flowability, compressibility and content uniformity. It is desirable that, in a population of particles, not more than 10%, preferably not more than 5% of the particles; should have a particle size greater than 850 µ; and not more than 20%, preferably not more than 15% of the particles should have a particle size lesser than 150 µ. Such a population of particles generally has good flowability and content uniformity. The fractional lobe processor used for hot melt fragmentation can provide a product conforming to these requirements without any need for further sieving or size reduction.

In an embodiment, the disclosure relates to a method of forming fragments within a fractional lobe processor comprising feeding an active substance and one or more excipient(s) into the barrel of the fractional lobe processor; softening or melting at least one excipient and/ or active substance to form a viscous mass or melt; and simultaneously fragmenting and cooling the viscous mass or melt to obtain cooled particles followed by collecting the cooled particles from the processor; wherein the collected particle population has a particle size distribution such that, not more than 10% of the particles have a particle size greater than 850 μ and not more than 15% of the particles have a particle size lesser than 150 μ.

The fractional lobe processor for Hot Melt Fragmentation comprises an intake zone for receiving one or more excipient(s) suitable for oral dosage along with one or more active pharmaceutical ingredient(s) (API), a melt zone for softening at least one excipient and/or API to form a viscous mass or melt, a fragmenting zone for simultaneously fragmenting and cooling the viscous mass into cooled fragments and an outlet for recovering the cooled fragments from the processor.

The fractional lobe processor for Hot Melt Fragmentation is provided with suitable heating and cooling means on barrels of the fractional lobe processor for Hot Melt Fragmentation to heat or cool the barrels as desired. Any suitable cooling means known to those skilled in the art can be used. Examples of such cooling means include but are not limited to a fluid cooling jacket surrounding the barrel, liquid nitrogen and dry ice.

The melt zone comprises one or more FLE(s) listed above. In accordance with an embodiment, one or more FLE(s) are placed in the beginning of the fragmenting zone. One or more conveying elements are placed towards the end of the fragmenting zone. Placement of the FLE(s) in the melt zone allows processing of the APIs and/or the meltable excipient(s) at lower barrel temperatures. Further, the shear imparted by the FLE(s) in the melt zone helps to prevent or reduce the degradation or unwanted by-products of the material being processed. Also, the FLE(s) in the melt zone is advantageous in processing of molten material having low viscosity as compared to the integer lobe kneading elements in the melt zone. The FLE(s) also considerably minimize formation of a residue or a film on any surface of the fractional lobe processor in the melt zone and the fragmenting zone. The conveying elements assist in conveying cooled and fragmented particles to the outlet of the processor.

The fractional lobe processor for Hot Melt Fragmentation provides options of spatial and temporal control over work done on the material. There can be qualitative and quantitative control on the work done on the material being processed by selecting suitable FLE(s) as mentioned above, or process parameters such as screw speed and barrel temperature, or location of the FLE(s) in the screw configuration. As illustrated in the examples, it is possible to manipulate the length to diameter ratio of the processor by using the FLE(s).

In an embodiment, the fractional lobe processor has a screw configuration such that the intake zone comprises elements selected from a group consisting of SSV and SSV-3RSE elements and the melt zone comprises elements selected from a group consisting of 3DSA, MFE and FKB.

The screw configuration of the fractional lobe processor for hot melt fragmentation is such that, in the melt zone, at least one of the fractional elements has a first lobe defining a first tip angle, a second lobe defining a second tip angle, and a third lobe defining a third tip angle that is different from the first tip angle and the second tip angle.

Alternatively, the screw configuration of the fractional lobe processor for hot melt fragmentation is such that, at least one of the fractional elements in the melt zone has a continuous flight helically formed thereon having a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L'.

As another alternative, the screw configuration of the fractional lobe processor for hot melt fragmentation is such that, at least one of the fractional elements in the melt zone has a lead 'L' and at least one continuous flight helically formed thereon and, wherein the flight transforms at least once from a first non-integer lobe flight into a second non-integer lobe flight in a fraction of the lead 'L' and transforms back to the first non-integer lobe flight in a fraction of the lead 'L.'

In an embodiment, the fragmenting zone comprises one or more mixing elements. The mixing elements can be completely self-wiping elements. The use of at least one mixing element, along with simultaneous cooling permits the process to be applied to all excipients, including fatty acids, glyceryl behenate and waxes; and particularly stearic acid. Examples of the mixing element include the elements having low screw-barrel and screw-screw clearances of below 250 microns.

The excipient includes one or more excipients that serve as a carrier, a filler or a binder for the API component. The excipients could be any pharmaceutical grade material in its solid, semisolid or liquid form. The excipients may be crystalline, amorphous or semi-crystalline in nature. Excipients may be hydrophilic, amphiphilic or lipophilic. Excipients may be ionic or non-ionic. Excipients may be celluloses such as ethyl cellulose, hydroxypropyl cellulose, hydroxypropyl methyl cellulose. Excipient may also be polyethylene glycol, polyethylene oxide, polyvinyl pyrrolidone, copovidone, polyvinyl acetate or polymethacrylates. Excipients may include plasticizers and/or processing aids such as triethyl citrate, triacetin, propylene glycol, dibutyl sebacate, diethyl phthalate, glycerol monostearate. In particular, excipients may also be fatty acids such as stearic acid, glyceryl behenate and waxes. The excipients may also be additives like drug-release modifiers, disintegrants and super disintegrants, thickening agents, bulking agents, binders, flow aids, sweeteners, and anti-oxidants. The choice of excipients may be determined by the person skilled in the art based on properties of the API, desired properties of the pharmaceutical composition and amenability to fragmentation. The formation of the melt or viscous mass involves heating the mixture of the API component and excipient component above the softening or glass transition temperature Tg or the melting point of the excipient(s).

The formation of the melt or viscous mass involves heating the mixture of the API component and excipient component above the softening or glass transition temperature Tg or the melting point of the excipient(s).

The temperature and the screw configuration in the melt zone are such that only the excipient(s) or both the excipient(s) as well as the API soften or melt to form the viscous mass or melt. The excipient(s) or the API(s) used could be either crystalline having sharp melting point or amorphous form with a Tg or softening temperature or semi-crystalline with a broad melting point and Tg. Depending on the application and processing temperature, the excipient(s) or both the excipient(s) and the API could be in the form of a continuous viscous mass or melt within the fractional lobe processor for Hot Melt Fragmentation followed by fragmentation while cooling within the processor.

The applications of the fractional lobe processor for Hot Melt Fragmentation include formation of pharmaceutical particles that have one or more of the desired properties not limited to bio-availability enhancement, controlled release, and taste-masking. Unlike the conventional Hot Melt Extrusion, (also popularly known as HME) where a hot viscous mass is extruded out which is then cooled and particle size reduced post extrusion; in the current hot melt fragmentation process the cooling of the viscous mass or melt is done within the fractional lobe processor for Hot Melt Fragmentation to a temperature at or below the softening temperature or Tg or melting point of the excipient(s) to initiate simultaneous solidification and fragmentation of the viscous mass or melt. This gives cooled solid fragments that are directly obtained from the fractional lobe processor. The solidified mass is scraped off the barrel surfaces by the screw elements in the fragmenting zone and fragmented. The cooling and simultaneous fragmentation of the viscous mass or melt at a temperature ranging from Tg or melting point to below the Tg or melting point enables production of increasingly smaller fragments. It is preferred that the cooling be continued to sufficiently below the Tg or melting point of the carrier to promote the solidification process, enable further milling and fragmentation and achieve the required particle size distribution.

In the simplest process, a mixture is typically a solid mixture of powders or granules. This mixture is converted into a melt or viscous mass in the melt zone. The viscous mass or melt is then fragmented while cooling in the fragmenting zone to obtain cooled solid fragments of homogeneous dispersion of the API component and the excipient component.

In accordance with an embodiment, the temperature of the melt in the fragmenting zone should be kept below the softening temperature or Tg or the melting point of the excipient. Lesser cooling in the fragmenting zone results in larger fragments. Greater cooling in the fragmenting zone forms finer fragments. In accordance with an embodiment, a cooling gradient of the melt towards the exit of the fractional lobe processor for Hot Melt Fragmentation may be maintained.

In accordance with an embodiment, the fractional lobe processor for Hot Melt Fragmentation is a co-rotating twin screw extruder. In an example, the processor has a length to diameter ratio less than 60. In a particular example, the length to diameter ratio is 40.

The fractional lobe processor for Hot Melt Fragmentation and the process allow manufacturing of a pharmaceutical composition having controlled particle size in accordance with the desired application. Depending on the desired drug dosage form, fragments of various size ranges can be obtained. For example-fine fragments for forming oral suspensions, medium to coarse fragments for forming tablets or filling into capsules may be obtained.

In accordance with an embodiment a population of multiparticulates by a hot melt fragmentation process having the particle size distribution is such that more than 75% particles are in the size range of 150-850 µ, less than about 10% of the particles are of size greater than 850 µ and less than 15% of the particles are of size less than 150 µ can be consistently obtained. This particle size distribution is highly desirable for good flow characteristics and content uniformity.

Further, the fractional lobe processor for Hot Melt Fragmentation and the process allow manufacturing of fragments or granules directly without any additional downstream processing. Thus, fragments can be obtained for tablet compression, capsule filling and for preparing sprinkles or suspensions for oral administration without involving complex downstream auxiliary equipment.

Hot Melt Extrusion

Hot melt extrusion (HME) is the process of applying heat and pressure to melt a material (polymer) and force it though an orifice to obtain extrudates. The FLP can be used for the HME to produce polymer products of uniform shape and density. To shape the extrudate as per requirements, different types of dies can be used at the exit, such as slit or film and sheet dies, annular dies, open profile dies, hollow profile dies or combinations thereof.

In case of pharmaceutical applications, the fractional lobe processor for Hot Melt Extrusion comprises an intake zone for receiving one or more excipient(s) suitable for oral dosage along with one or more Active Pharmaceutical Ingredient(s) (API), a melt zone for melting at least one excipient to form a viscous mass or melt and an outlet with a die for recovering the viscous mass or melt (extrudate) from the fractional lobe processor for Hot Melt Extrusion.

The zones represent sections of the screw configuration designed to perform a specific function like conveying, melting and mixing and the like. Accordingly, corresponding barrel sections are referred to herein as zones. For example, in the intake zone the screw configuration has special elements such as SSV or SSV-3RSE suitable for intake of feed and conveying.

The fractional lobe processor for Hot Melt Extrusion is provided with suitable heating and cooling means on barrels of the fractional lobe processor to heat or cool the barrels as desired. Any suitable cooling means known to those skilled in the art can alternatively be used. Examples of such cooling means include but are not limited to a fluid cooling jacket surrounding the barrel, liquid nitrogen and dry ice.

The melt zone comprises one or more FLE(s). The choice of the FLE(s) depends upon factors such as desired attributes of the output. Other factors taken into consideration would be Tg of the API (active ingredient) or excipient, amount of work to be done on the material etc. The FLE such as 3DSA, MFE may be suitable for pharmaceutical grade materials to be processed.

In accordance with an embodiment, the fractional lobe processor for Hot Melt Extrusion further comprises a mixing zone between the melt zone and the outlet. The mixing zone may also comprise one or more FLE(s).

The excipient includes one or more excipients that serve as a carrier, a filler or a binder for the API component. The excipients could be any pharmaceutical grade material in its solid, semisolid or liquid form. The excipients may be crystalline, amorphous or semi-crystalline in nature. Excipients may be hydrophilic, amphiphilic or lipophilic. Excipients may be ionic or non-ionic. Excipients may be celluloses such as ethyl cellulose, hydroxypropyl cellulose, hydroxypropyl methyl cellulose. Excipient may also be polyethylene glycol, polyethylene oxide, polyvinyl pyrrolidone, copovidone, polyvinyl acetate or polymethacrylates. Excipients may include plasticizers and/or processing aids such as triethyl citrate, triacetin, propylene glycol, dibutyl sebacate, diethyl phthalate, glycerol monostearate. In particular, excipients may also be fatty acids such as stearic acid, glyceryl behenate and waxes. The excipients may also be additives like drug-release modifiers, disintegrants and super disintegrants, thickening agents, bulking agents, binders, flow aids, sweeteners, and anti-oxidants. The choice of excipients may be determined by the person skilled in the art based on properties of the API, desired properties of the pharmaceutical composition and amenability to fragmentation. The formation of the melt or viscous mass involves heating the mixture of the API component and excipient component above the softening or glass transition temperature Tg or the melting point of the excipient(s).

The temperature and the screw configuration in the melt zone are such that only the excipient(s) or both the excipient(s) as well as the API melt to form the viscous mass or melt. The excipient(s) or the API(s) used could be either crystalline having sharp melting point or amorphous form with a Tg or softening temperature or semi-crystalline with a broad melting point and Tg.

In accordance with an embodiment, the fractional lobe processor for Hot Melt Extrusion is a co-rotating twin screw extruder. The fractional lobe processor for Hot Melt Extrusion can be a fully wiping processor. In an example, the fractional lobe processor for Hot Melt Extrusion has a length to diameter ratio less than 60. In a particular example, the length to diameter ratio is 40. Additional downstream auxiliary components can also be used with the fractional lobe processor for Hot Melt Extrusion. Examples of such components include water baths, air knives, conveyor belts, strand-cutters and spoolers. Further, pelletizers can be used for cutting the extrudate into smaller sizes suitable for capsule filling.

The fractional lobe processor for Hot Melt Extrusion is suitable for processing, semi-crystalline polymers having a narrow processing temperature range, ensuring that crystallization does not occur-during the process. In the processor, this crystallization can be avoided by carefully controlling the processing temperature of each barrel of the fractional lobe processor separately. The processor is particularly useful to address the problem of feeding of pellets that can be too large or asymmetrical in shape by use of the shovel elements SSV and SSV-3RSE.

For pharmaceutical applications, the polymers are thermoplastic, stable at the processing temperatures and chemically compatible with the active ingredient/s or drug/s during extrusion. Water soluble polymers are usually chosen from among polymers such as polyethylene glycol and polyvinylpyrrolidone.

Placement of the FLE(s) in the melt zone allows processing of the APIs and/or meltable excipient(s) at lower barrel temperatures. Further, the shear imparted by the FLE(s) in the melt zone is optimum, which helps to prevent or reduce the degradation or unwanted by-products of the material being processed. A suitable example of such shear sensitive API that can be processed with minimal impurity in the output, is Ritonavir. Use of the FLE(s) in the melt zone eliminates shear peaks and ensures a uniform transfer of energy to polymers being processed, giving the capability and the control to work with such sensitive materials. Also, the FLE(s) in the melt zone is advantageous in processing of molten material having low viscosity as compared to the integer lobe kneading elements. It also minimizes formation of residue or film on any surface in the melt zone.

The fractional lobe processor for Hot Melt Extrusion provides options of spatial and temporal control over work done on the material. There can be qualitative and quantitative control on the work done on the material being processed by suitably selecting the FLEs as mentioned above, or process parameters such as screw speed and barrel temperature, or location of the FLE(s) in the screw configuration. As illustrated in the examples it is possible to manipulate the length to diameter ratio by using the FLE(s).

In an embodiment, the fractional lobe processor has a screw configuration such that the intake zone comprises elements selected from a group consisting of SSV and SSV-3RSE elements and the melt zone comprises elements selected from a group consisting of 3DSA, MFE and FKB.

The screw configuration of the fractional lobe processor for hot melt extrusion is such that, in the melt zone, at least one of the fractional elements has a first lobe defining a first tip angle, a second lobe defining a second tip angle, and a third lobe defining a third tip angle that is different from the first tip angle and the second tip angle.

Alternatively, the screw configuration of the fractional lobe processor for hot melt extrusion is such that, at least one of the fractional elements in the melt zone has a continuous flight helically formed thereon having a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L'.

As another alternative, the screw configuration of the fractional lobe processor for hot melt extrusion is such that, at least one of the fractional elements in the melt zone has a lead 'L' and at least one continuous flight helically formed thereon and, wherein the flight transforms at least once from a first non-integer lobe flight into a second non-integer lobe flight in a fraction of the lead 'L' and transforms back to the first non-integer lobe flight in a fraction of the lead 'L.'

The disclosed process can be widely applied in the plastic, rubber and food industries. It can also be used to manufacture medical devices or prepare precursors for medical devices such as subcutaneous and intraocular implants, contact lenses and intravaginal rings. Further, the disclosed fractional lobe processor for Hot Melt Extrusion and the process can be used to compound active pharmaceutical ingredients with polymers to enhance bioavailability. The fractional lobe processor for Hot Melt Extrusion significantly reduces the residence time of material in the processing zone and is advantageous to extrude materials such as polyurethanes which are heat- and moisture-sensitive and time-sensitive. The fractional lobe processor for Hot Melt Extrusion is specialized in the processing of a variety of materials including solids (powders, granulates, flours), liquids, slurries, and possibly gases. Extruded products are typically plastic compounds, chemically modified polymers, textured food and feed products, cellulose pulps, etc. In pharmaceutical applications, the processor is suitable for the preparation of Fixed dose combinations (FDC) approved by drug regulatory authorities for the treatment for AIDS. In food processing, the processor offers several advantages such as continuous high temperature cooking in short time, high productivity by reduction in downtime and material losses. The process can be suitably adjusted to process a variety of raw materials to produce a wide range of food products.

The invention is further explained by the following non-limiting examples.

EXAMPLES

Example A: Hot Melt Fragmentation for Azithromycin extended release fragments

| Quantitative composition | | | |
|---|---|---|---|
| S. No | Ingredient | mg/tab | % w/w |
| 1 | Azithromycin hydrate (Equivalent to 2000 mg Azithromycin) | 2125.75 | 39.99 |
| 2 | Glyceryl behenate | 3188.63 | 68.01 |
| | Total | 5314.38 | 100 |

Figure 2:
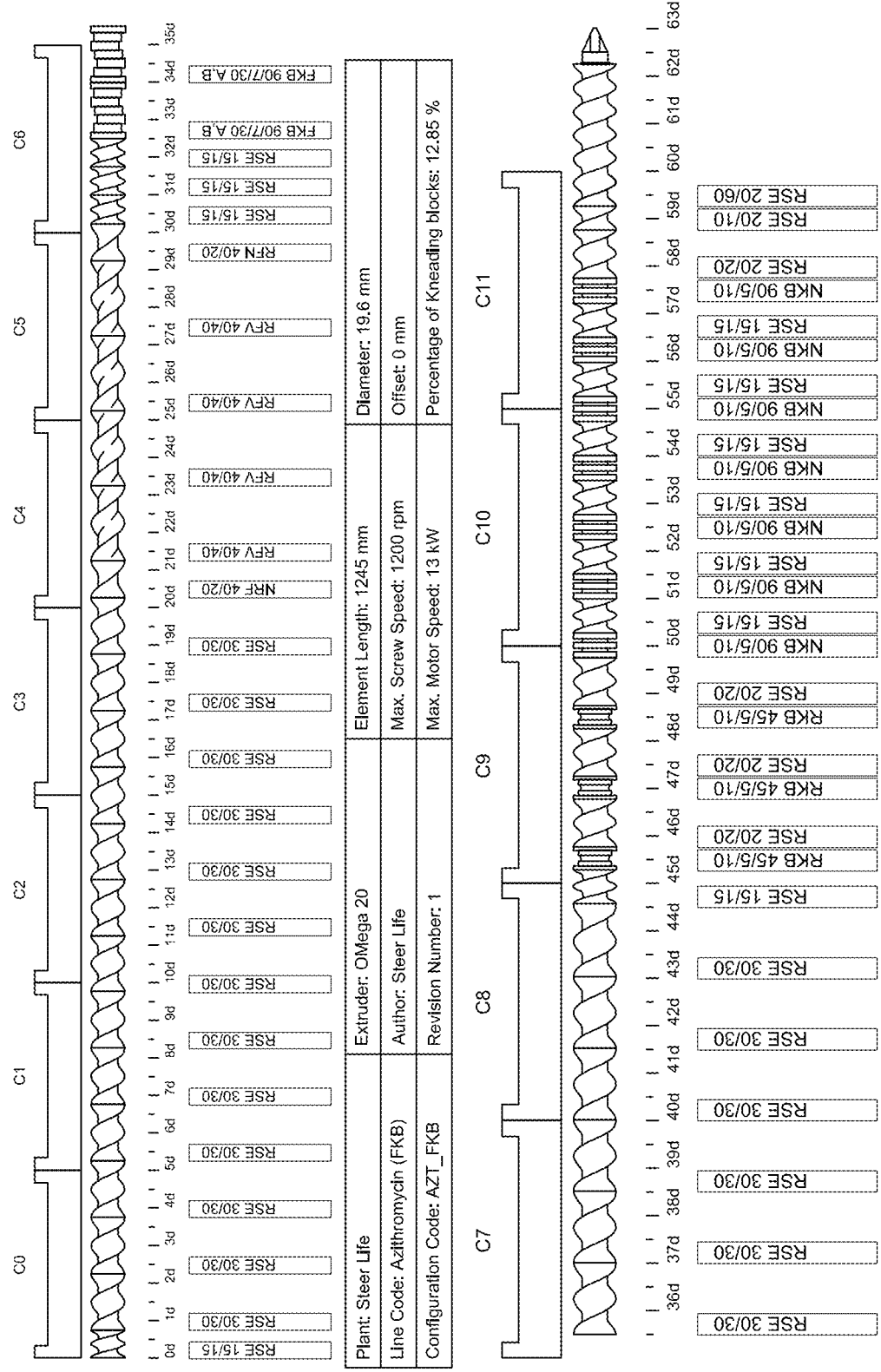
FIGS. 2-4 depict screw configurations of Fractional Lobe Processors (FLP) in accordance with various embodiments of the present disclosure.

Procedure: Both the ingredients were passed through mesh #40, mixed and processed in the fractional lobe processor for Hot Melt Fragmentation having screw configuration as depicted in FIG. 2.

| Processing parameters: | |
|---|---|
| L1D | 40 |
| Feed rate | 1.0 kg/h |
| Screw speed | 250 rpm |
| Torque | 21 Nm |
| Length of the FLE(s) in the melt zone | FKB 90/7/30-60 mm = 7.5% of screw configuration |
| Length of fragmenting elements | RKB 45/5/10-30 mm; NKB 90/5/10-70 mm |

| Temperature of barrels: | | | | | | | | | | | |
|---|---|---|---|---|---|---|---|---|---|---|---|
| Barrel No. | B1 C0 | B2 C1 | B3 C2 | B4 C3 | B5* C4 | B6 C5 | B7 C6 | B8 C7 | B9 C8 | B10 C9 | B11 C10 | B12 C11 |
| Set Temp. | NA | 30 | 30 | 30 | 30 | 30 | 95 | 95 | 15 | 15 | 15 | 15 |
| Actual Temp. | 32 | 30 | 29 | 28 | 30 | 30 | 96 | 95 | 24 | 19 | 19 | 18 |
| | | | | | Intake zone | | Melt zone | | Conveying zone | Fragmenting zone | | Discharge or outlet |

*Feed from 5$^{th}$ barrel

Note: For carrying out the experiments, only B5 to B12 of a standard co-rotating twin screw processor Omega 20 P Steer Engineering Private Limited, was used.

Results:

| Characterization of fragments: | | |
|---|---|---|
| Mesh No | % Weight retained | Cumulative % wt. retained |
| 20 | 3.55 | 3.55 |
| 40 | 21.17 | 24.72 |
| 60 | 22.12 | 46.84 |
| 80 | 10.82 | 57.66 |
| 100 | 8.61 | 66.27 |
| 120 | 3.87 | 70.14 |
| Base | 29.15 | 99.29 |

Derived properties:

Bulk density (g/cc)=0.40; Tap density (g/cc)=0.56; Compressibility index (%)=28.0; Hausner's ratio 1.38

Observations

As compared to the examples of PCT application no. PCT/1N2014/000358, the HMF process could be carried out at a shorter L/D with the fractional lobe processor. Also, the positioning of FLE(s) at the beginning of the melt zone provided for efficient melt and mixing of the material being processed.

EXAMPLES FOR HOT MELT FRAGMENTATION

| Composition: | | | |
|---|---|---|---|
| S.No. | Ingredient | mg/Unit | 'Yow/w |
| 1 | Potassium chloride | 751.57 | 74.1 |
| 2 | Hydrogenated vegetable oil (Lubritab ®) | 263.04 | 25.9 |
| | Total | 1014.61 | 100.0 |

Procedure:

Potassium chloride (less than 90 μm), Lubritab® (less than 250 μm) were mixed manually and processed using Twin Screw Processor having screw configuration devoid of fractional lobe elements and Fractional Lobe Processor at varying process parameters.

Process parameters:

Machine-Omega 20, Steer Engineering Private Limited; Length /Diameter=60; Feed rate=9.6 kg/h; Screw Speed (rpm) 250, 500 and 1000

| Temperature profile of barrels for twin screw processor and fractional lobe processor: | | | | | | | | | |
|---|---|---|---|---|---|---|---|---|---|
| B1 | B2 | B3 | B4 | B5 | B6 | B7 | B8 | B9 | B10 |
| 23 | 30 | 80 | 80 | 10 | 10 | 10 | 10 | 10 | 10 |

COMPARATIVE EXAMPLES—HOT MELT FRAGMENTATION WITH TWIN SCREW PROCESSOR WITHOUT FRACTIONAL ELEMENTS

Comparative Example 1:

| Screw Configuration | | | | | | | | | | | |
|---|---|---|---|---|---|---|---|---|---|---|---|
| Element | RSE 15/15 | NRF 40/20 | RFV 40/40 | RFN 40/20 | RSE 20/20 | RKB 45/5/20 | RKB 45/5/15 | RSE 20/20 | NKB 90/5/20 | NKB 90/5/10 | RSE 20/20 | RSE 30/30 |
| No. of elements | 1 | 1 | 4 | 1 | 9 | 1 | 3 | 18 | 1 | 1 | 10 | 5 |

NKB = Neutral Kneading Block, RKB = Right handed kneading block, RSE = Right handed screw element, RFV = Right handed Shovel element, RFN = Right handed transition element, NKB = Neutral Kneading Block Comparative Example 2

| Element | RSE 15/15 | NRF 40/20 | RFV 40/40 | RFN 40/20 | RSE 20/20 | RKB 45/5/20 | RKB 45/5/15 | RSE 20/20 | NKB 90/5/20 | NKB 90/5/10 | RSE 20/20 | NKB 90/5/20 | NKB 90/5/10 | RSE 20/20 | RSE 30/30 |
|---|---|---|---|---|---|---|---|---|---|---|---|---|---|---|---|
| Screw Configuration | | | | | | | | | | | | | | | |
| No. of elements | 1 | 1 | 4 | 1 | 9 | 1 | 3 | 18 | 1 | 1 | 2 | 1 | 1 | 8 | 4 |

Comparative Example 3

| Element | RSE 15/15 | NRF 40/20 | RFV 40/40 | RFN 40/20 | RSE 20/20 | RKB 45/5/20 | RKB 45/5/15 | RSE 20/20 | RKB 45/5/20 | RKB 45/5/10 | RSE 20/20 | RKB 45/5/20 | RKB 45/5/10 | RSE 20/20 | RSE 30/30 |
|---|---|---|---|---|---|---|---|---|---|---|---|---|---|---|---|
| Screw Configuration | | | | | | | | | | | | | | | |
| No. of elements | 1 | 1 | 4 | 1 | 9 | 1 | 3 | 18 | 1 | 1 | 2 | 1 | 1 | 8 | 4 |

EXAMPLES—HOT MELT FRAGMENTATION USING FRACTIONAL LOBE PROCESSOR

Example 1

| Elements | 3 RSE 15/15 | SSV 40/40 | SSV3RSE 40/20 | 3RSE 30/60 | 3 RSE 20/40 | 3 DSA 20/40 | 3 RSE 20/60 | 3 RSE 20/40 | FKB 30/7/30 | 3RSE 20/40 | 3 RSE 15/15 | 3 RSE 40/40 | Spacer 5 mm |
|---|---|---|---|---|---|---|---|---|---|---|---|---|---|
| No. of elements | 1 | 4 | 1 | 2 | 2 | 2 | 5 | 1 | 1 | 5 | 2 | 3 | 1 |
| Zones | Intake Zone | | | Melt zone | | | Cooling and fragmentation zone | | | | Discharge Zone | | |

Example 2

| Elements | 3 RSE 15/15 | SSV 40/40 | SSV3RSE 40/20 | 3RSE 30/60 | 3 RSE 20/40 | 3 DSA 20/40 | 3 RSE 20/60 | 3 RSE 20/40 | FKB 30/7/30 | 3RSE 20/40 | FKB 30/7/30 | 3RSE 20/40 | 3RSE 20/60 | 3RSE 30/60 | 3RSE 40/40 |
|---|---|---|---|---|---|---|---|---|---|---|---|---|---|---|---|
| No. of elements | 1 | 4 | 1 | 2 | 2 | 2 | 5 | 1 | 1 | 1 | 1 | 1 | 1 | 1 | 3 |
| | Intake zone | | | Melt zone | | | Cooling and fragmentation zone | | | | | | Discharge zone | | |

Example 3

| Elements | 3 RSE 15/15 | SSV 40/40 | SSV 3RSE 40/20 | 3RSE 30/60 | 3 RSE 20/40 | 3 DSA 20/40 | 3 RSE 20/60 | 3 RSE 20/40 | FKB 30/7/30 | 3RSE 20/40 | FKB 30/7/30 | 3RSE 20/40 | FKB 30/7/15 | 3RSE 20/40 | 3RSE 40/40 | Spacer 10 mm |
|---|---|---|---|---|---|---|---|---|---|---|---|---|---|---|---|---|
| No. of elements | 1 | 4 | 1 | 2 | 2 | 2 | 5 | 1 | 1 | 1 | 1 | 2 | 1 | 4 | 1 | |
| | Intake zone | | | Melt zone | | | Cooling and fragmentation zone | | | | | | Discharge zone | | | |

Observations:

Fragmentation using fractional lobe processor results in a particle size distribution wherein majority of particles are in the desired range of particle size (i.e. 150-850 μ). In the Fractional Lobe Processor, increasing the number of FLE's in the fragmenting zone or changing the screw speed does not alter the particle size distribution significantly. Whereas in case of twin screw processor with NKB elements, increasing the number of elements has a significant effect on the particle size distribution. In case of twin screw processor with RKB elements, changing the screw speed particle size distribution changes significantly.

Example 4. Metformin HCL Dual Matrix Multiparticulates

| Formula: | |
|---|---|
| Ingredients | % w/w |
| Metformin Hydrochloride | 77.0 |
| Hydroxypropy methyl cellulose K100M | 8.461 |
| Lubritab (Hydrogenated vegetable oil) | 13.846 |

All the ingredients were weighed and dispensed. Metformin Hydrochloride was delumped. All other excipients were passed through mesh #40 and mixed and blended with the Metformin Hydrochloride.

| Screw configuration for Omega 20P (STEER Engineering Private Limited): | | | | | | | | | | | |
|---|---|---|---|---|---|---|---|---|---|---|---|
| Elements | CHS 15/15 | SSV 40/40 | 3RSE SSV40/20 | 3RSE 20/60 | 3RSE 40/40 | 3DSA 40/40 | 3DSA 20/40 | 3DSA 40/40 | 3RSE 40/40 | 3RSE 30/60 | 3RSE 40/40 | 3RSE 20/60 |
| No | 1 | 4 | 1 | 2 | 1 | 1 | 3 | 1 | 3 | 5 | 1 | 3 |
| Zones | Intake zone | | | Melt zone | | | | | Cooling and sizing zone | | | ** |

** Discharge zone

| Barrel Temperature Profile (° C.): | | | | | | | | | | | | |
|---|---|---|---|---|---|---|---|---|---|---|---|---|
| Barrel No | B1 | B2 | B3 | B4 | B5 | B6 | B7 | B8 | B9 | B10 | B11 | B12 |
| Temp (° C.) | 30 | 30 | 30 | 120 | 120 | 120 | 120 | 20 | 20 | 20 | 20 | 20 |

Processing Parameters: Feed rate-12.0 Kg/hour, Screw Speed-500 rpm

Results: Particle size distribution Sieve no. (% Cumulative Wt. Retained): #20 (10.85); #40(30.38); #60(56.79); #80(79.30); #100(92.96); Median Diameter=300 μ

Parameters for Granules: Bulk density (g/cc)=0.412, Tapped Density (g/cc)=0.544, Compressibility index (%)=24.324, Hausner's Ratio=1.321 Free flowing directly compressible multiparticulate population of metformin with less than 11% particles>850 μ and less than 8% particles<150 μ was obtained using fractional lobe processor.

Example 5. Ibuprofen multiparticulates

| Formula: | |
|---|---|
| Ingredients | % w/w |
| Ibuprofen | 100 |

Ibuprofen API was weighed and dispensed and passed through #10 to remove any lumps.

| Screw configuration for Omega 20P (STEER Engineering Private Limited): | | | | | | | | | | | | |
|---|---|---|---|---|---|---|---|---|---|---|---|---|
| Elements | CHS 15/15 | Spacer 8 mm | SSV 40/40 | 3RSE SSV 40/20 | 3RSE 20/60 | 3RSE 40/40 | 3DSA 40/40 | 3DSA 20/40 | 3DSA 40/40 | 3RSE 30/60 | 3RSE 40/40 | 3RSE 20/60 |
| No | 1 | 1 | 4 | 1 | 2 | 1 | 1 | 3 | 1 | 5 | 1 | 3 |
| Zones | Intake Zone | | | | Melt zone | | | | Cooling and sizing zone | | | ** |

** Discharge zone

| Barrel Temperature (° C.): | | | | | | | | | | | | |
|---|---|---|---|---|---|---|---|---|---|---|---|---|
| Barrel No | B1 | B2 | B3 | B4 | B5 | B6 | B7 | B8 | B9 | B10 | B11 | B12 |
| Temp (° C.) | 30 | 30 | 100 | 90 | 90 | 15 | 15 | 15 | 15 | 15 | 15 | 15 |

Processing Parameters: Feed Rate-20.0 kg/hour, Screw Speed-800 rpm

Results: Particle size distribution Sieve no. (% Cumulative Wt. Retained):

20 (5.33); #30 (10.76); #40 (18.40); #60 (42.44); #80 (70.22); #100 (81.27); Median Diameter=240 μ

Parameters for Granules: Bulk density (g/cc)-0.508; Tapped Density (g/cc)-0.620; Compressibility index (%)-18.182; Hausner's Ratio-1.222 Free flowing directly compressible granules of Ibuprofen were obtained without any added excipients using fractional lobe processor.

EXAMPLES FOR HOT MELT EXTRUSION

Example 6: Hot melt extrusion of Lopinavir and Ritonavir

| Quantitative Composition: | | | |
|---|---|---|---|
| S.No. | Ingredient | mg/unit | % w/w |
| 1 | Lopinavir (Equivalent to 200 mg Lopinavir) | 209.76 | 18.7 |
| 2 | Ritonavir (Equivalent to 50 mg Ritonavir) | 50.32 | 4.5 |
| 3 | Copovidone | 780.24 | 69.6 |
| 4 | Sorbitan monolaurate | 60.0 | 5.4 |
| 5 | Colloidal silicon dioxide | 20.0 | 1.8 |
| | Total | 1120.32 | 100 |

Procedure: Lopinavir, Ritonavir and Copovidone were passed through #40 screen and mixed manually with #60 passed colloidal silicon dioxide. This blend was granulated using Sorbitan monolaurate and processed in the processor.

Figure 3:
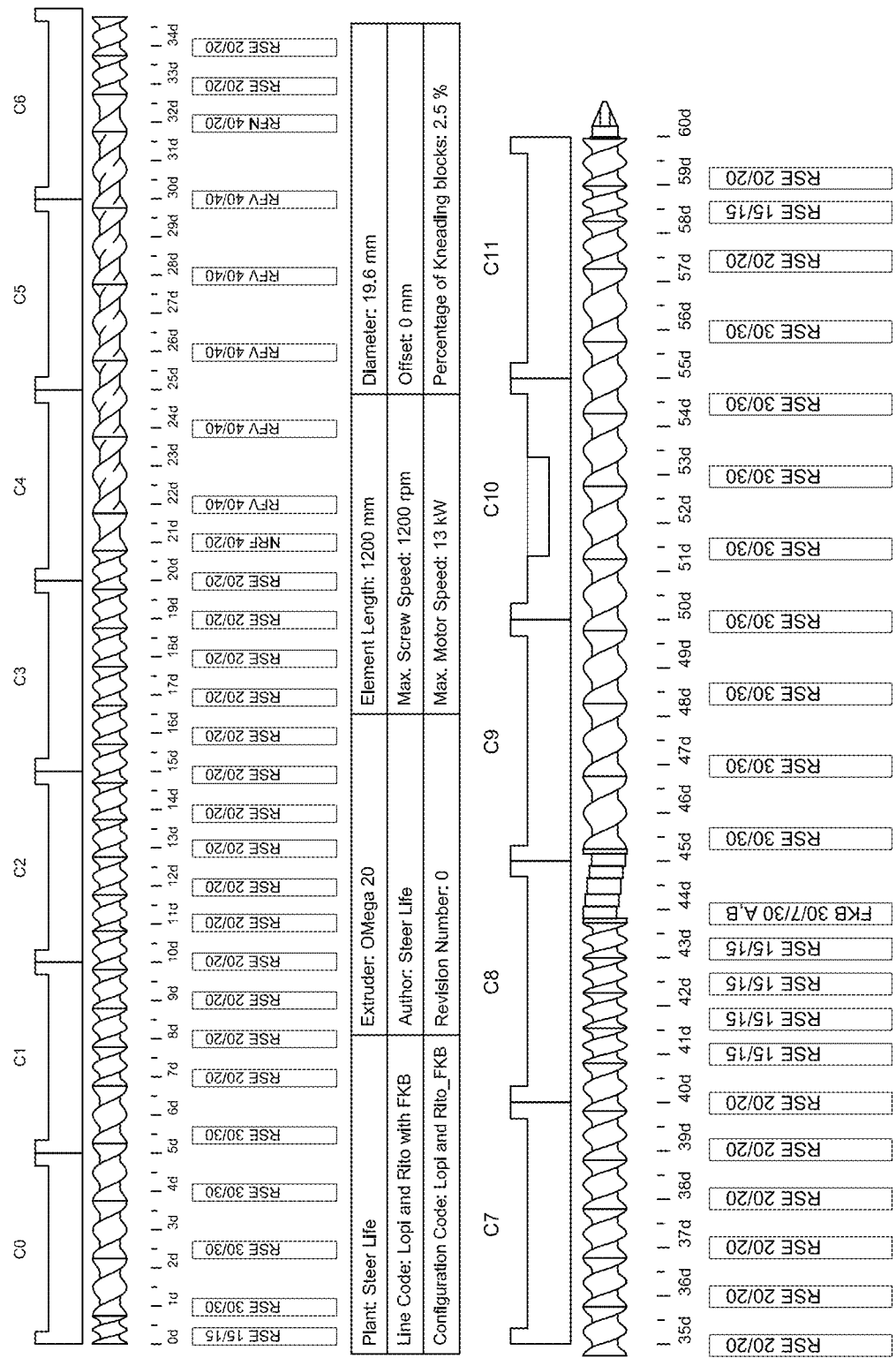

Processing parameters:

Twin screw processor-Omega 20P Steer Engineering Private Limited; L/D-40; Feed rate-12 Kg/h; Screw speed-500 rpm; Torque-192 Nm; Vacuum-100 mm Hg; Length of mixing elements in the melt zone-FKB 30/7/30—30 mm; Percentage of FLE(s) 3.75% Please refer to FIG. 3 for the screw configuration of the fractional lobe processor for Hot Melt Extrusion used for this example.

| Temperature of barrels: | | | | | | | | | | | | |
|---|---|---|---|---|---|---|---|---|---|---|---|---|
| Barrel | B1 C0 | B2 C1 | B3 C2 | B4 C3 | B5* C4 | B6 C5 | B7 C6 | B8 C7 | B9 C8 | B10 C9 | B11# C10 | B12 C11 | Die |
| Set Temp. | NA | 30 | 30 | 30 | 30 | 30 | 50 | 80 | 100 | 120 | 120 | 120 | 120 |
| Actual Temp. | 32 | 30 | 29 | 28 | 30 | 30 | 50 | 80 | 102 | 121 | 120 | 120 | 120 |
| | Inactive zone | | | Intake zone | | Melting and mixing zone | | | | | | |

Vacuum at B11

Figure 4:
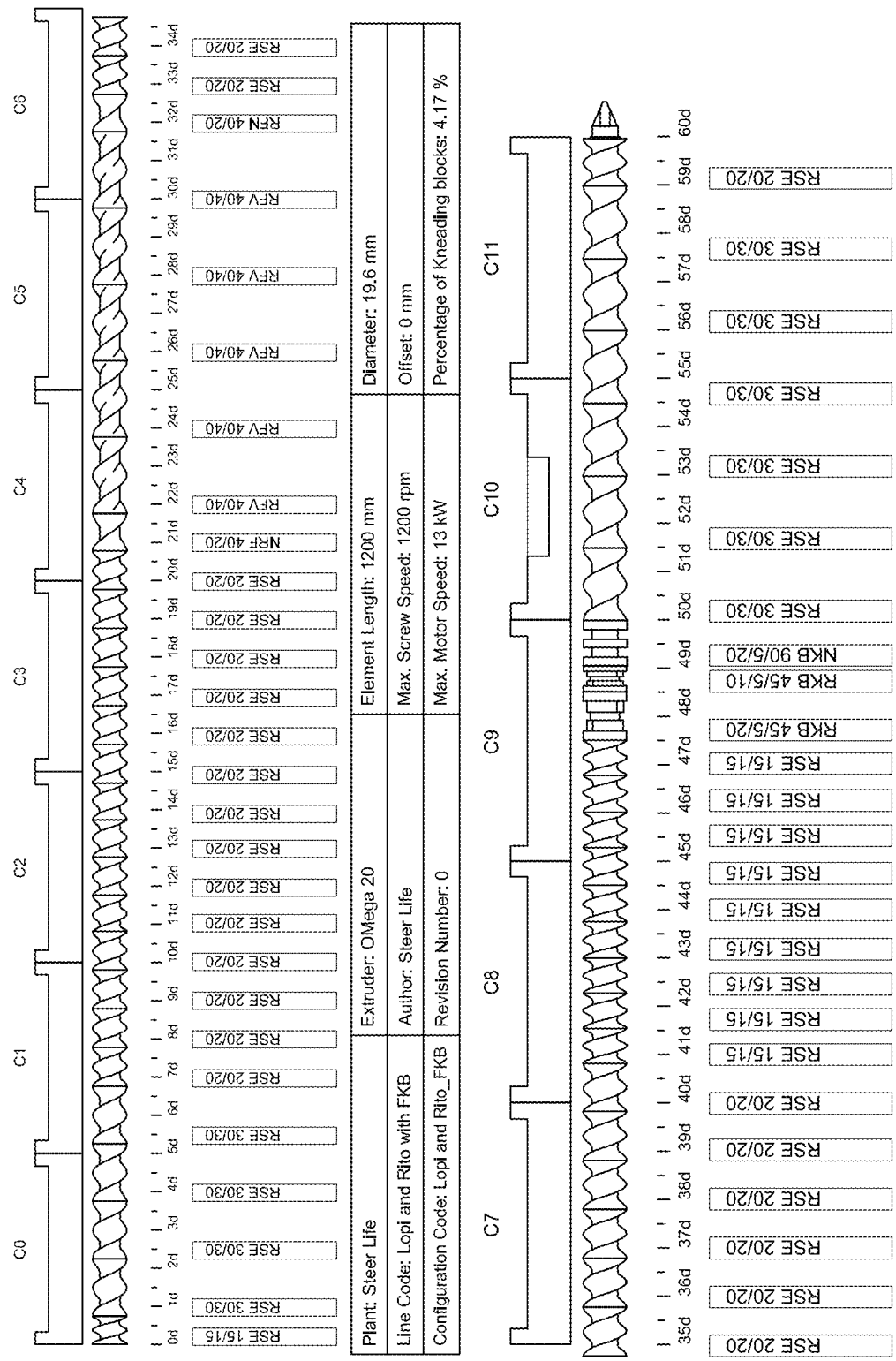
Figure 5A:
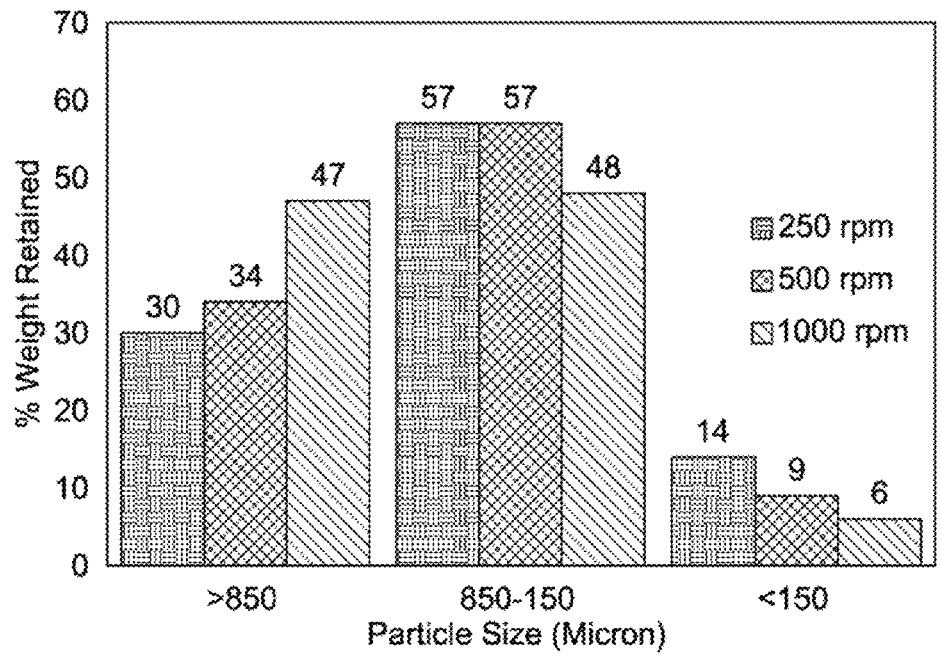
FIGS. 5A-5F show results of hot melt fragmentation using fractional lobe processor.
Figure 5B:
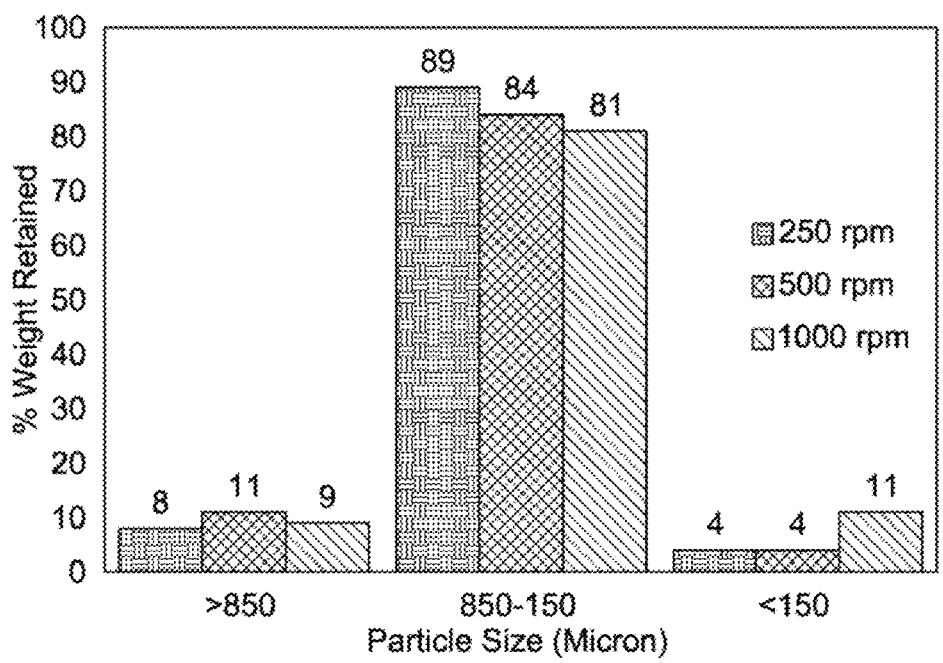
Figure 5C:
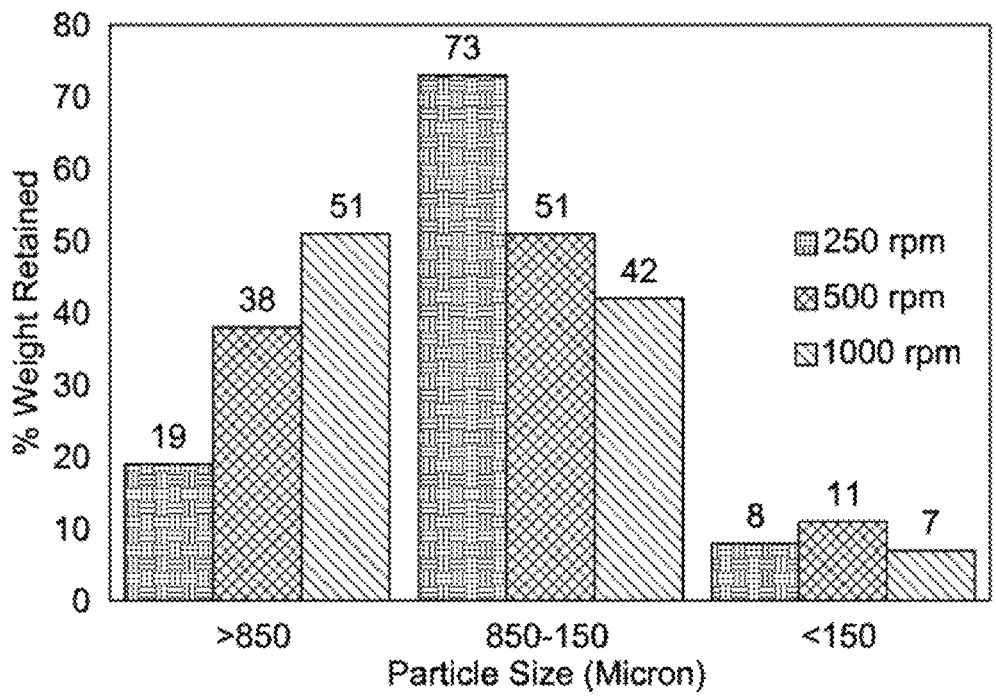
Figure 5D:
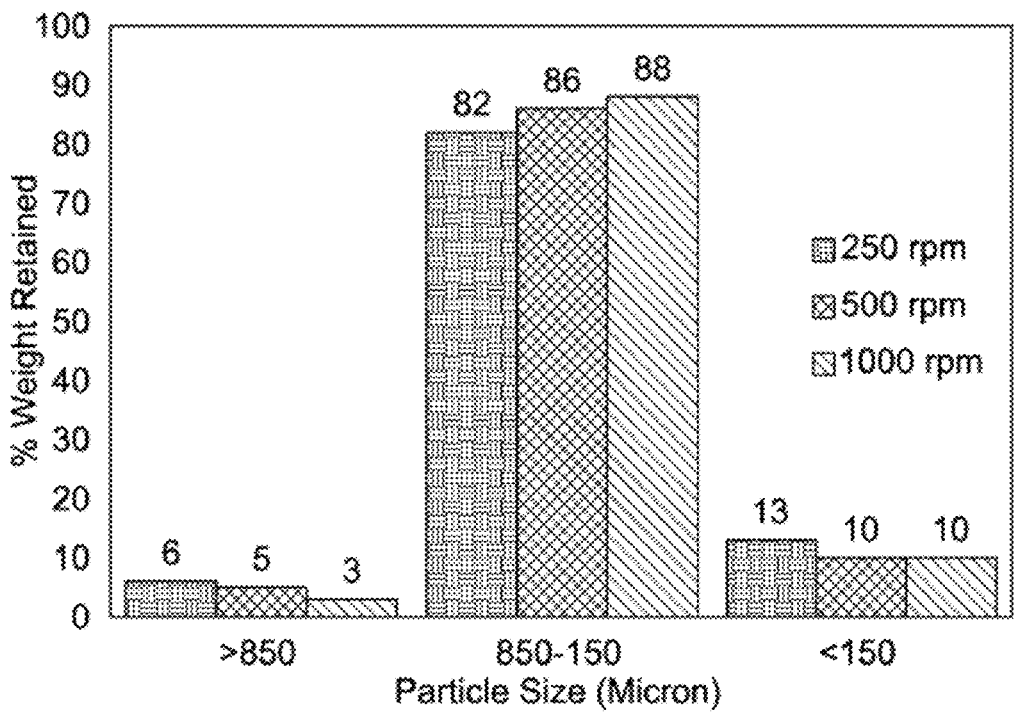
Figure 5E:
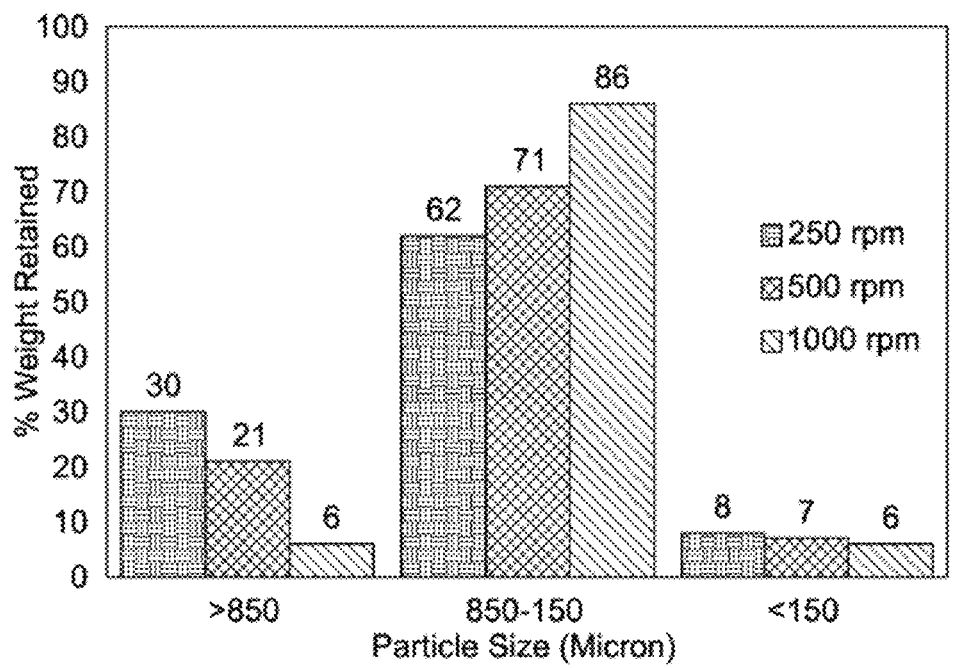
Figure 5F:
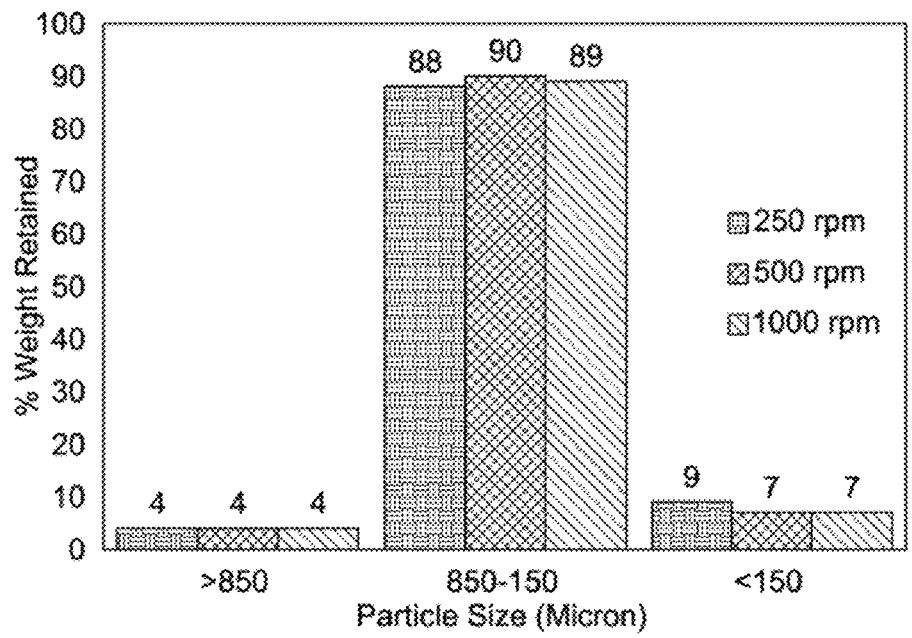
Figure 6:
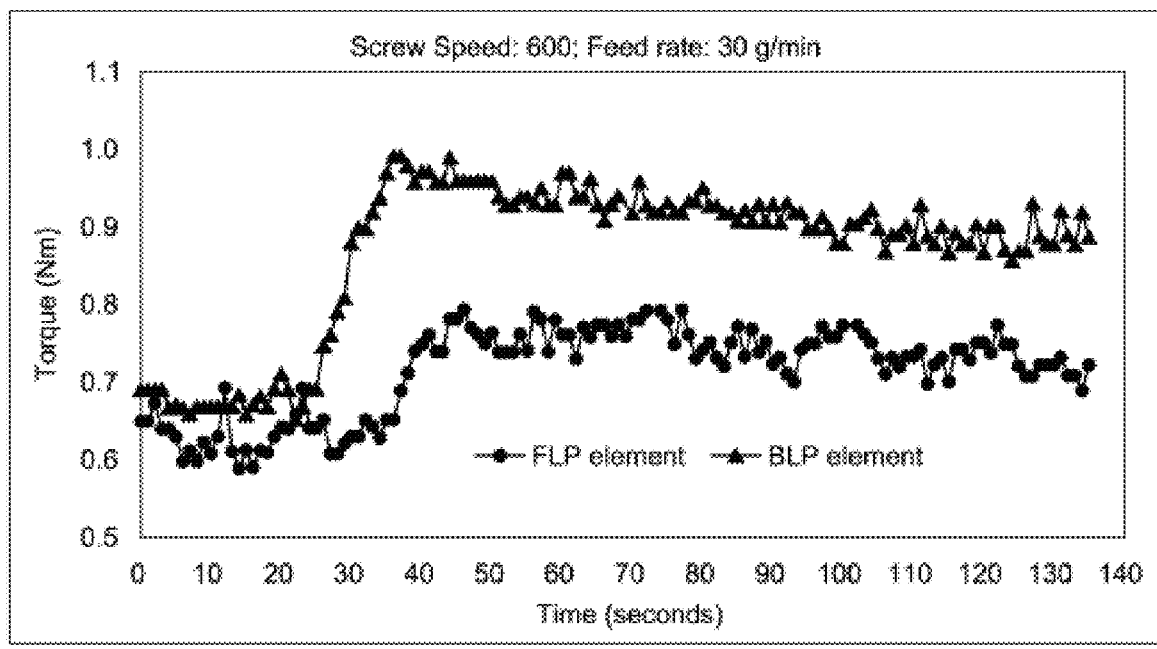
FIG. 6 is Graph 1 showing torque readings captured and graphically represented. Screw speed: 600; Feed rate: 30 g/min.
Figure 7:
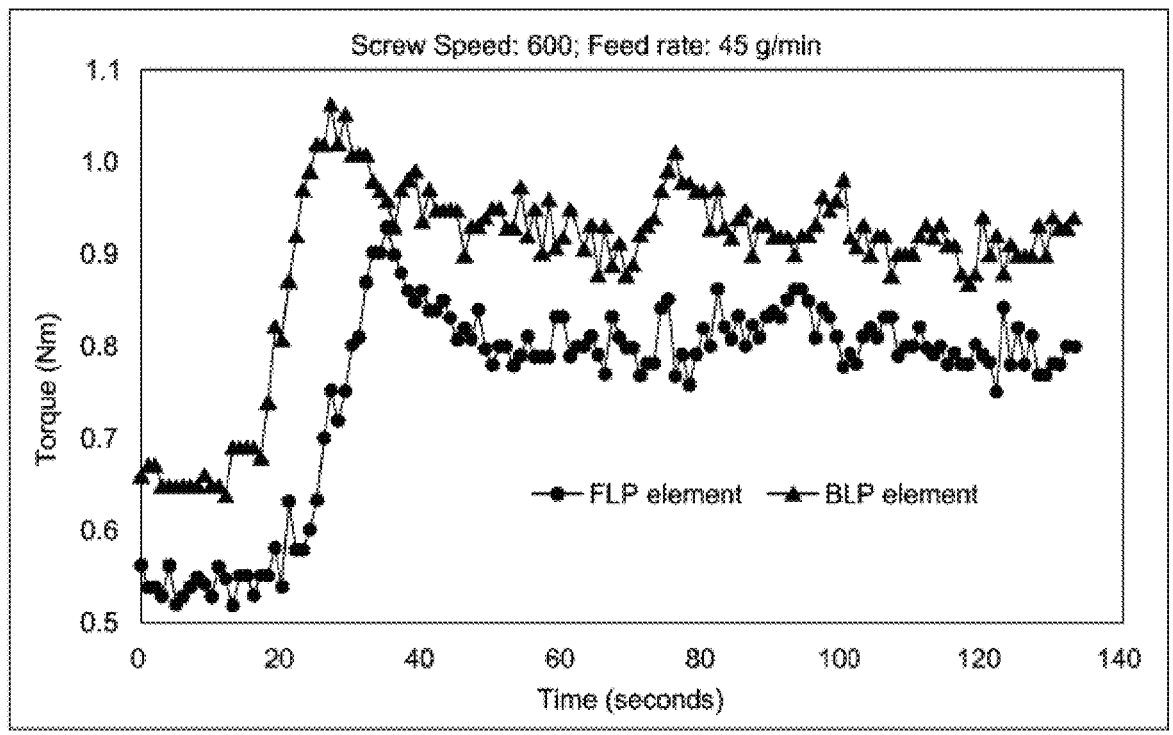
FIG. 7 is Graph 2 showing torque readings captured and graphically represented. Screw speed: 600; Feed rate: 45 g/min.

Comparative Example 4: Without FLE(s):

Composition, procedure and temperature profile of the barrels was the same as Example 4. Screw configuration of the processor used for this example is mentioned in FIG. 4.

Processing parameters: Twin screw processor-Omega 20P; L/D=40; Feed rate=12 kg/h; Screw speed=500 rpm; Torque=60-65%; Vacuum-Not applied Observations: Clear extrudates were obtained with output as high as 12 kg per hour in both examples. Generally clear extrudates can be considered as an indicator of uniform dispersion of drug, with low impurity content. However, it was observed that only one fractional kneading block of length 30 mm in the melt and mixing zone could provide the same results as that of a combination of integer lobe elements of length 50 mm. It indicates that the use of FLE(s) can be explored for further reducing the residence time of the processed material in the processor.

Example 7: Fractional Lobe Processor Hot Melt Extrusion of Ritonavir

| Composition: | |
|---|---|
| Ingredients | % w/w |
| Ritonavir | 18.62 |
| Copovidone | 73.98 |
| Sorbitan monolaurate | 5.60 |
| Colloidal silicon dioxide | 1.80 |
| Total | 100.00 |

Procedure:

Ritonavir, Copovidone, Colloidal silicon dioxide were mixed and co-sifted through #30 mesh. This mixture is granulated with Sorbitan monolaurate and then extruded in a 20 mm diameter co-rotating Fractional lobe Processor (Omega 20P, STEER Engineering Pvt. Ltd. Bengaluru). In all the examples, the processor Length/Diameter (L/D) was 60. The processing was done by feeding at feeding or intake zone (processing L/D-40) using the screw configuration specified in Table A and vacuum of 400 mm/Hg was applied during the process. The function of each zone is specified in Table B. Feed rate and screw speed were varied as are specified in Table C.

TABLE A

| Screw configuration for 60 L/D: | | | | | | | | | | | | | |
|---|---|---|---|---|---|---|---|---|---|---|---|---|---|
| Screw elements | RSE-15/15 (CHS) | RSE-30/30 | NRF-40/20 | RFV-40/40 | RFN-40/20 | Spacer-5 mm | 3RSE-40/40 | 3RSE-30/60 | 3RSE-20/40 | 3DSA 20/40 | 3 RSE 40/40 | 3RSE-30/60 | 3RSE-20/40 |
| Nos. | 1 | 13 | 1 | 5 | 1 | 1 | 1 | 2 | 3 | 1 | 3 | 1 | 1 |
| | Non-functional zones | | | Intake zone | | | Melt Zone | | | | | Discharge zone | |

TABLE B

| Barrel Temperature profile | | | | | | | | | | | | | |
|---|---|---|---|---|---|---|---|---|---|---|---|---|---|
| Barrel number | B1 | B2 | B3 | B4 | B5 | B6 | B7 | B8 | B9 | B10 | B11* | B12 | Die |
| Barrel Temp (° C.) | 30 | 30 | 30 | 30 | 30 | 30 | 50 | 80 | 100 | 120 | 120 | 120 | 120 |

*Vacuum applied

TABLE C

| Parameter for Fractional lobe processing of Ritonavir | | | | | |
|---|---|---|---|---|---|
| Parameters | Example-I | Example-II | Example-III | Example-IV | Example-V |
| Screw speed (rpm) | 500 | 700 | 700 | 900 | 900 |
| Feed rate (Kg/hr) | 12 | 12 | 18 | 20 | 20 |
| Vacuum pressure (mm /Hg) | 400 | 400 | 400 | 400 | 400 |
| Torque during processing (%) | 47 | 66 | 55 | 76 | 76 |

TABLE D

Organic Impurities of the milled Hot Melt Extrudates

| Name of the Impurity | Pre mix | Example-I | Example-II | Example-III | Example-IV | Example-V | USP (NMT %) |
|---|---|---|---|---|---|---|---|
| N-Deacylvaline ritonavir | BQL | BQL | BQL | BQL | BQL | BQL | 0.20 |
| Hydroxy ritonavir | BQL | BQL | BQL | BQL | BQL | BQL | 0.30 |
| Hydantoin amino alcohol | BQL | 0.28 | 0.71 | 0.48 | 0.42 | 1.25 | 2.60 |
| Ritonavir hydroperoxide | ND | ND | ND | ND | ND | ND | 0.20 |
| Geo-isomer | ND | ND | ND | ND | ND | ND | 0.20 |
| Oxazolidinone derivative | ND | ND | ND | ND | ND | 0.059 | 0.30 |
| Any individual unspecified degradation product | ND | 0.05 | BQL | BQL | BQL | BQL | 0.20 |
| Total impurities | 0.00 | 0.33 | 0.71 | 0.48 | 0.42 | 1.31 | 3.5 |

BQL—Below quantification limit (0.05%);
NMT—Not more than;
USP: United States Pharmacopoeia;
ND—Not Detected The impurities in the trials were well below the USP limit and also total impurities did not exceed 1.31. This can be attributed to no stagnation of material in the processing zones of the fractional lobe processor.

EXPERIMENTAL EXAMPLE 1: EFFECT OF GEOMETRY

Trials were performed in a Twin screw processor with a provision for measurement of torque every 30 seconds. The feeder was calibrated to give a wide range of feed rates. Also, the processor screw speed was calibrated using a rotameter. Fenofibrate was used as the drug with Kollidon VA64 as the polymer in a 1:3 ratio of drug: polymer.

A real-time comparison was done between Right handed kneading element (RKB 30/7/30) and a tri-lobe fractional lobe element (3DSA 30/30) with respect to the torque requirements at different feed rates using the blend of Fenofibrate: Kollidon VA64 (1:3). The torque was captured using Human Machine Interface for every 30 seconds. A run time of 2 minutes was kept for each trial and torque values obtained were graphically represented and compared.

Processor Details: L/D=9; Do/Di=1.80; STEER Engineering Private Limited

Screw Configuration A:

| Element | RSE-20/60 | RKB-30/7/30 | RSE-20/30 | RSE-20/60 |
|---|---|---|---|---|
| No. | 1 | 1 | 1 | 1 |

RKB = Right handed kneading block

Screw Configuration B:

| Element | RSE-20/60 | 3DSA 30/30 | RSE-20/30 | RSE-20/60 |
|---|---|---|---|---|
| No. | 1 | 1 | 1 | 1 |

The Set of experiments performed were as follows:

| Screw Speed | Feed Rate (g/min) | |
|---|---|---|
| (rpm) | 3DSA 30/30 | RKB 30/7/30 |
| 600 | 30 | 30 |
|  | 40 | 40 |
|  | 55 | 55 |

Observations:

Observations:

| Feed Rate (g/min) | Observations | |
|---|---|---|
|  | RKB 30/7/30 | 3DSA 30/30 |
| 30 | Complete molten extrudates | Complete molten extrudates |
| 45 | Partial melting was observed | Complete molten extrudates |
| 55 | Incomplete melting was observed | Incomplete melting was observed |

Conclusion:

Based on the torque profiles, it can be observed that at lower feed rate (30 and 45 g/min), FLE viz. 3DSA has lower torque requirement and there is complete melting of the material processed. This indicates that the Fractional lobe element can process the material at higher feed rate with lower torque requirement. Further increasing the feed rate to 55 g/min both the elements could not melt the material, specifying saturation on mechanical energy input and may be demanding for higher thermal energy for the quantity of material being per unit time. Thus, based on the study design with varying feed rate, 3DSA (Fractional Lobe element) gives a better product and higher throughput and lower torque profiles compared to RKB (Bilobed element).

We claim:
1. A fractional lobe processor comprising
a barrel with heating and cooling means having two parallel intersecting bores of equal diameter, wherein the center distance between the two bores is lesser than the diameter of the bore;
a shaft coupled with a plurality of screw elements to form a screw within each bore, wherein the screws are intermeshing, and wherein the screws form at least three zones within the barrel, the zones comprising:
an intake zone comprising at least one element defining an acute angle undercut on each intermeshing screw for receiving a feed comprising an active substance and/or an excipient;
a melt zone consisting of only fractional lobe elements for melting the active substance and/or an excipient to form a viscous mass or melt; and
a discharge zone;
wherein the melt zone is located before the discharge zone and after the intake zone;
wherein the melt zone has a plurality of fractional lobe elements on each shaft;
wherein at least one of the fractional elements in the melt zone has a lead 'L' and at least one continuous flight helically formed thereon and, wherein the flight transforms at least once from a first non-integer lobe flight into a second non-integer lobe flight in a fraction of the lead 'L' and transforms back to the first non-integer lobe flight in a fraction of the lead 'L'.

2. The fractional lobe processor according to claim 1, wherein the melt zone comprises of at least two different fractional lobe elements on each intermeshing screw.

3. The fractional lobe processor according to claim 1, wherein between the melt zone and the discharge zone, the screws form a zone that comprises of a plurality of 3lobe right hand screw elements on each intermeshing screw.

4. The fractional lobe processor according to claim 1, wherein at least one-third length of each intermeshing screw comprises of fractional lobe elements from intake zone to the discharge zone.

5. The fractional lobe processor according to claim 1, wherein at least one of the fractional elements in the melt zone has a first lobe defining a first tip angle, a second lobe defining a second tip angle, and a third lobe defining a third tip angle that is different from the first tip angle and the second tip angle.

6. The fractional lobe processor according to claim 1, wherein at least one of the fractional elements in the melt zone has a continuous flight helically formed thereon having a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L'.

7. A method of hot melt extrusion comprising the steps of:
a) introducing a feed comprising an active substance and/or an excipient into the intake zone of the fractional lobe processor according to claim 1,
b) passing the feed through a melt zone consisting of only fractional elements, which is set at a temperature above the melting or softening temperature of the active substance and/or the excipient for melting the active substance and/or an excipient to form a viscous mass or melt;
c) passing the viscous mass or melt through a discharge zone towards a die located at the end of the discharge zone;
d) extruding the viscous mass or melt through the die.

8. The method according to claim 7, wherein the fractional lobe processor has a screw configuration such that the intake zone comprises one or more elements selected from a group consisting of SSV and SSV-3RSE elements and the melt zone comprises one or more elements selected from a group consisting of 3DSA, MFE and FKB.

9. A method of hot melt fragmentation comprising the steps of:
a) introducing a feed comprising active substance and/or an excipient into the intake zone of the fractional lobe processor according to claim 1,
b) passing the feed through a melt zone consisting of only fractional elements, which is set at a temperature above the melting or softening temperature of the active substance and/or the excipient for melting the active substance and/or the excipient to form a viscous mass;
c) passing the viscous mass through a fragmenting zone for simultaneously cooling and fragmenting the viscous mass inside the barrel to form cooled multiparticulates;
d) passing the cooled multiparticulates through the discharge zone towards the exit located at the end of the discharge zone; and
e) collecting the cooled multiparticulates.

10. The method according to claim 9, wherein the fractional lobe processor has a screw configuration such that the intake zone comprises one or more elements selected from a group consisting of SSV and SSV-3RSE elements and the melt zone comprises one or more elements selected from a group consisting of 3DSA, MFE and FKB.

11. A process for preparation of a population of multiparticulates having the particle size distribution such that more than 75% particles are in the size range of 150-850 µ, less than about 10% of the particles are of size greater than 850 µ and less than 15% of the particles are of size less than 150 µ, by the method of hot melt fragmentation, according to claim 10.

* * * * *